(12) United States Patent
Eriksen et al.

(10) Patent No.: US 8,357,100 B2
(45) Date of Patent: Jan. 22, 2013

(54) MANAGING FLOW/VOLUME LOOP INFORMATION

(75) Inventors: Morten Eriksen, Oslo (NO); Øivind Enger, Bergen (NO)

(73) Assignee: Volusense AS, Oslo (NO)

( * ) Notice: Subject to any disclaimer, the term of this patent is extended or adjusted under 35 U.S.C. 154(b) by 766 days.

(21) Appl. No.: 12/395,411

(22) Filed: Feb. 27, 2009

(65) Prior Publication Data

US 2010/0222693 A1    Sep. 2, 2010

(51) Int. Cl.
*A61B 5/08* (2006.01)
(52) U.S. Cl. .................................................. 600/538
(58) Field of Classification Search .................. None
See application file for complete search history.

(56) References Cited

U.S. PATENT DOCUMENTS

| 5,456,264 A | 10/1995 | Series et al. |
| 5,984,872 A | 11/1999 | Vriend |

OTHER PUBLICATIONS

Johnson et al. Relation Between Limiting Exhalation Flow Rate and Lung Volume. IEEE Transactions on Biomedical Engineering, Mar. 1987, vol. BME-34, No. 3, pp. 257-258.*
Jarriel W S et al: "A Nonlinear Regression Analysis of Nonlinear, Passive-Deflation Flow-Volume Plots", Mar. 1993, pp. 175-182, vol. 15, No. 3, Pediatric Pulmonology, section Materials and Methods, p. 179, XP002595396; ISSN: 8755-6863.
McKiernan B C et al: "Tidal Breathing Flow-Volume Loops in Healthy and Bronchitic Cats", Nov.-Dec. 1993, pp. 388-393, vol. 7, No. 6, Journal of Veterinary Internal Medicine American College of Veterinary Internal Medicine, section Materials and Methods, LNKD-PUBMED: 8114037, XP002595395; ISSN: 0891-6640.
Rusnak M et al: "Centre of gravity of the area beneath the flow/volume curve", 1990, pp. 326-329, vol. 50, No. 5, Studia Pneumologica et Phtiseologica, Chechoslovaca; XP002595397, ISSN: 0371-2222.
English Translation of Rusnak M et al: "Centre of gravity of the area beneath the flow/volume curve", 1990, pp. 326-329, vol. 50, No. 5, Studia Pneumologica et Phtiseologica, Chechoslovaca; XP002595397, ISSN: 0371-2222.
Schmalisch G et al: "Differences in tidal breathing between infants with chronic lung diseases and healthy controls", Sep. 8, 2005, p. 36, vol. 5, No. 1, BMC Pediatrics, Biomed Central, London, GB, section Materials and Methods, LNKD-DOI:10.1186/1471-2431-5-36, XP021005023; ISSN: 1471-2431.
WIPO, International Search Report, dated Aug. 16, 2010, (5 pages), for corresponding International Application No. PCT/IB2010/000481.

* cited by examiner

*Primary Examiner* — Louise Humphrey
(74) *Attorney, Agent, or Firm* — Mintz Levin Cohn Ferris Glovsky and Popeo, P.C.

(57) ABSTRACT

Embodiments of the present invention provide methods of extracting optimal information from a flow/volume loop concerning the patient's respiratory condition by examining the overall shape of the space under the flow/volume loop's expiration portion. In some embodiments, this is done with reference to the center of mass of that space. In some embodiments, this is done with reference to the area of that space. Some embodiments are significantly less affected by random/statistical variations and/or noise within the measurement system than existing methods.

15 Claims, 6 Drawing Sheets

MANAGING FLOW/VOLUME LOOP INFORMATION

TECHNICAL FIELD

Some embodiments disclosed herein relate generally to managing information related to flow/volume loops.

BACKGROUND

Respiratory disease is a common and significant problem in both the United States and throughout the world. Obstructions generally make expiration slower and/or more difficult as more air is exhaled from the lungs or during the latter part of expiration. The obstruction can stem from the constriction of the airways during respiration, inflammation and edema of the walls of the terminal bronchi, or narrowing of the trachea or the throat. Types of respiratory disease include diseases of the lung, bronchial tubes, pleural cavity, upper respiratory tract, trachea, and of the nerves and muscles of breathing.

An important step in monitoring for and managing such diseases, as well as less severe respiratory conditions, involves measuring flow rate and/or the volume of air moving into and out of the patient's lungs. Methods of measuring such flow data include several standard spirometry methods. One illustrative spirometry method includes covering a patient's mouth and nose and channeling his/her breathing through a tube to a meter that measures the speed of sound as it propagates through the moving air. The effect that the moving air has on sound wave speed is indicative of an airflow rate. Another method involves a pneumotachometer in which a grid or mesh provides a small amount of resistance to the air as it flows through the grid. The pressure difference across the grid is measured, and that measurement provides information indicative of an airflow rate.

Methods of measuring such volume data include enclosing a patient entirely in a tank, with only his/her head extending out of the tank. An airtight seal is then provided around the neck and a gauge is incorporated into the tank for measuring displaced air as the patient's lungs expand and contract. The displaced air measurements are indicative of inhaled/exhaled volume. Another method of measuring the volume of air moving into and out of a patient's lungs involves covering a patient's mouth and nose and channeling his/her breathing through a tube to a bellows or piston assembly. The air can cause the bellows or piston to mechanically displace, and the displacement can be measured and correlated to the inhaled/exhaled volume. Additionally, VoluSense, the assignee of the present invention, has developed one such method, which is disclosed in VoluSense's U.S. Pat. Nos. 6,374,667; 6,945,941; and 7,390,307. These patents are hereby incorporated by reference herein in their entirety.

Another important step in monitoring for and managing respiratory conditions involves analyzing and managing the collected flow data and volume data. As is discussed herein, an important tool for doing so is a flow/volume loop, which is a graph constructed from simultaneous recordings of exhaled volume and airway flow. Flow/volume loops can contain useful information related to a patient's respiratory condition. However, existing methods of analyzing and managing flow/volume loop information have a variety of drawbacks, which limit the quality and quantity of useful information that can be extracted from a flow/volume loop.

SUMMARY

Embodiments of the present invention provide methods of extracting optimal information from a flow/volume loop concerning the patient's respiratory condition by examining the overall shape of the space under the flow/volume loop's expiration portion. In some embodiments, this is done with reference to the center of mass of that space. In some embodiments, this is done with reference to the area of that space.

In some embodiments, the invention can involve a method of gathering data related to breathing patterns of a patient. The method can include acquiring flow data and volume data. Flow data can relate to a rate of air flow into and out of the patient's lungs. Volume data can relate to changes in volume of the patient's lungs. The method can include generating a flow/volume loop based on at least some of the flow data and at least some of the volume data. The flow/volume loop can have an expiration portion and an inspiration portion. The expiration portion can begin with a full-inhale point and end with a full-exhale point, which both lie along a zero-flow line. The method can include calculating an exhale pattern parameter based on an overall shape of an expiration space. The expiration space can be bounded by the expiration portion of the flow/volume loop and the zero-flow line. In some embodiments, a computer-readable medium can be programmed with instructions for causing a programmable processor to perform the method.

Embodiments of the present invention can provide one or more of the following advantages. Some embodiments are more repeatable, more predictable, and/or generally more reliable from one respiratory cycle to the next for a given patient, as compared with existing methods. In such embodiments, the patient's respiratory condition can be assessed by one who does not have the specialized experience of selecting the flow/volume loop of one cycle from among many as being representative of the patient's overall respiratory condition. Some embodiments provide more reliable results from one patient to another despite differences in size, age, and/or other characteristics, as compared with existing methods. Some embodiments are significantly less affected by random/statistical variations and/or noise within the measurement system than existing methods.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is illustrative in nature and is not intended to limit the scope, applicability, or configuration of the invention in any way. Rather, the following description provides practical illustrations for implementing exemplary embodiments of the present invention. Examples of constructions, materials, dimensions, and manufacturing processes are provided for selected elements, and all other elements employ that which is known to those of skill in the field of the invention. Those skilled in the art will recognize that many of the examples provided have suitable alternatives that can be utilized.

Figure 1A:
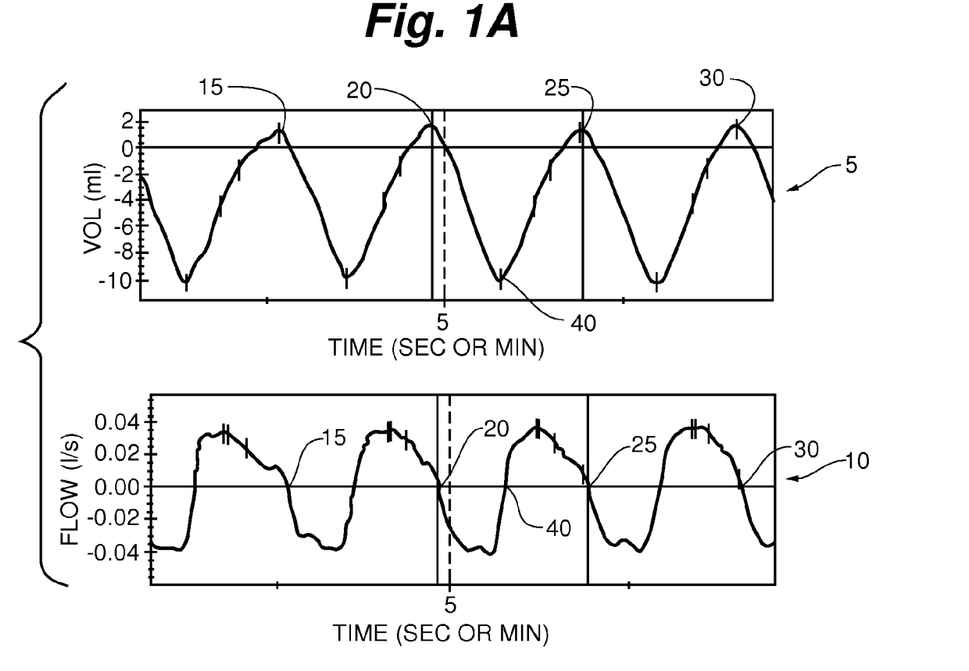
FIG. 1A is a plot of air flow (bottom) and exhaled air volume (top) vs. time for a healthy example patient.

FIG. 1A shows a plot 5 of the volume of air exhaled from a patient's lungs vs. time, as well as a plot 10 of air flow out of the patient's lungs vs. time. Three breathing cycles are shown. The first cycle begins at point 15 and ends at point 20. The second cycle begins at point 20 and ends at point 25. The third cycle begins at point 25 and ends at point 30.

As can be seen, airflow and exhaled volume are related to one another. Minimum and maximum volume values occur when the flow is equal to zero. Minimum volume values occur as the patient transitions from expiration to inspiration, and there is no airflow at that full-exhale transition point. Likewise, maximum volume values occur as the patient transitions from inspiration to expiration, and there is no airflow at that full-inhale point.

In the plots 5, 10 of FIG. 1A, the flow value is shown as positive when air is flowing out of the patient's lungs. Likewise, in plots 5, 10, the volume value is shown as increasing as air is exiting the patient's lungs. A similar plot could be constructed which considers airflow into the patient's lungs to be positive and which would result in a corresponding rise in volume when air entered the patient's lungs.

Volume data and flow data as shown in FIG. 1A can be acquired in a variety of ways. In a few embodiments, both volume and flow can be measured according to one of the techniques discussed above or according to other suitable techniques. In most embodiments, either volume or flow is measured, but not both. In such embodiments, whichever is not measured is calculated from that which is measured. Methods discussed herein that accord with embodiments of the present invention can use flow data and volume data regardless of how it is acquired.

Figure 1B:
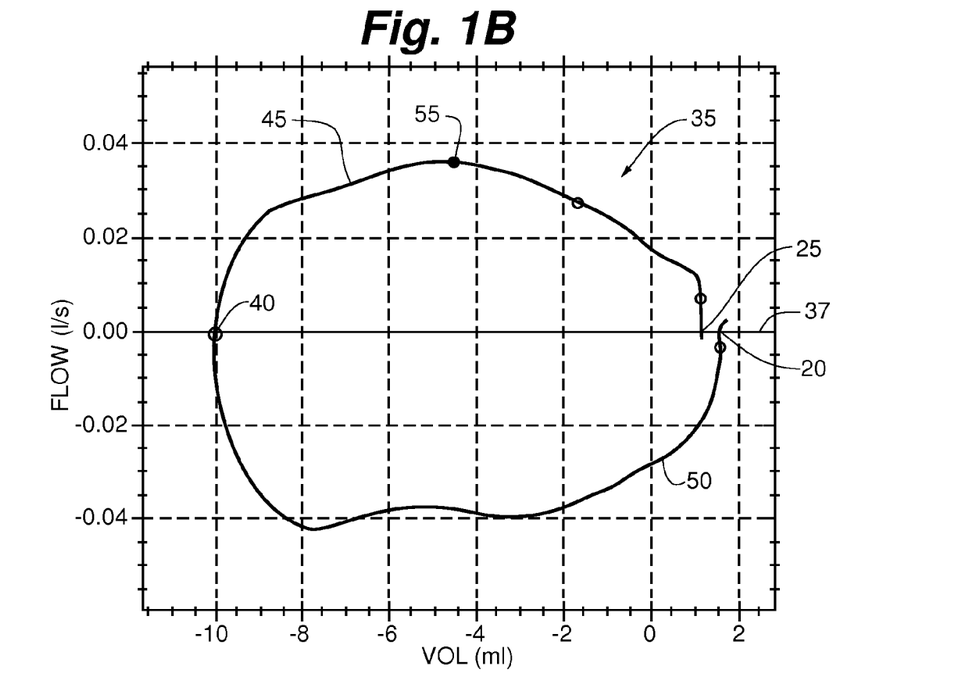
FIG. 1B is a flow/volume loop generated from flow data and volume data represented in the plot of FIG. 1A.

FIG. 1B shows a flow/volume loop 35, which plots volume data on the x-axis against flow data on the y-axis. The data shown is for the breathing cycle that begins with point 20 and ends with point 25 shown on FIG. 1A. Referring again to FIG. 1B, the flow/volume loop 35 includes a zero-flow line 37, which represents no airflow moving into or out of the lungs. As can be seen, the flow/volume loop 35 crosses the zero-flow line 37 at full-exhale point 20, full-inhale point 40, and again at full-exhale point 25. The lower part of the flow/volume loop 35 represents the patient's inspiration and is often referred to as the inspiration portion 50. The upper part of the flow/volume loop 35 represents the patient's expiration and is often referred to as the expiration portion 45.

The expiration portion 45 of the flow/volume loop 35 can contain especially important information regarding the respiratory patterns of the patient. The illustrative patient from which the flow data and volume data is taken in FIGS. 1A-1B is a normal, healthy patient, without an obstructive respiratory condition. This is evidenced by the generally symmetrical, domed shape of the expiration portion 45, which signifies that the patient breathes with generally the same degree of ease throughout expiration.

Figure 2A:
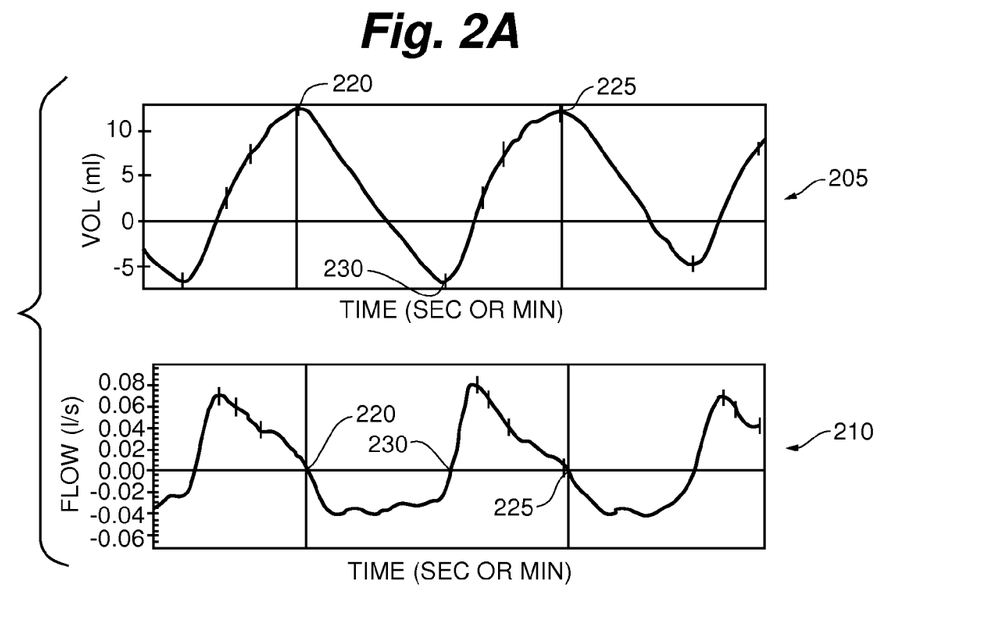
FIG. 2A is a plot of air flow and exhaled air volume vs. time for an example patient with an obstructive respiratory condition.
Figure 2B:
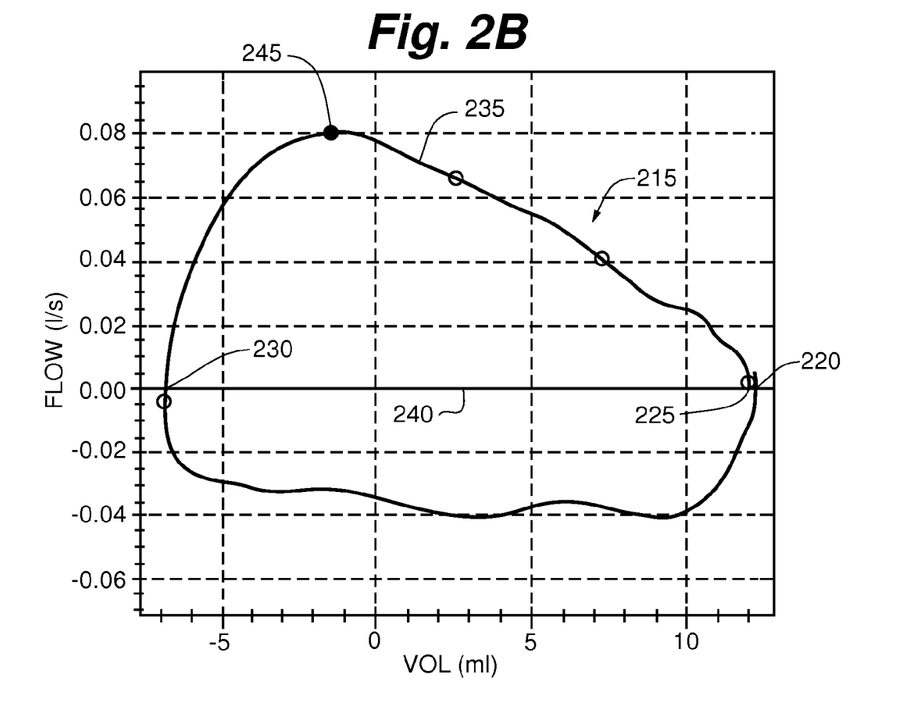
FIG. 2B is a flow/volume loop generated from flow data and volume data represented in the plot of FIG. 2A.

Like FIGS. 1A-1B, FIGS. 2A-2B show flow data and volume data vs. time and a corresponding flow/volume loop, respectively. FIG. 2A includes a plot 205 of exhaled volume vs. time, as well as a plot 210 of outward airflow vs. time. FIG. 2B shows a flow/volume loop 215, with flow data and volume data for the flow/volume loop 215 coming from the respiratory cycle beginning at point 220 and ending at point 225. Both points 220 and 225 are full-exhale points, which lie on a zero-flow line 240. The flow/volume loop 215 also crosses the zero-flow line 240 at full-inhale point 230.

As can be seen, the expiration portion 235 of the flow/volume loop 215 is shaped differently than that of FIG. 1B. The illustrative patient from which the flow data and volume data is taken in FIGS. 2A-2B has an obstructive respiratory condition (e.g., obstructive lung disease). This is evidenced by the shape of the expiration portion 235, which is unbalanced toward the left of the flow/volume loop 215. This means that the patient is able to breath easier during the first part of expiration and has greater difficulty breathing during the second part of expiration, indicating a narrowing of small airway conduits as the lungs collapse during expiration. With the information contained in the expiration portion of a flow/volume loop, a clinician is in a better position to assess the patient's respiratory condition.

Analyzing the expiration portion of a flow/volume loop in a quantitative manner can be important in assessing a patient's respiratory condition. Much can be gleaned from visually examining expiration portions—especially those that are relatively pronounced, like those of FIGS. 1B and 2B. But for most flow/volume loops, it is difficult for a clinician to accurately assess the patient's respiratory condition simply by looking at the expiration portion of the flow/volume loop.

Many methods for quantitatively analyzing flow/volume loops involve identifying the peak of the expiration portion. It can then be determined when during expiration does the peak airflow occur or what percentage of air volume was exhaled when airflow reached its peak. Under this method, when peak airflow occurs at the point when roughly half of the air volume has been exhaled, the patient likely does not have an obstructive respiratory condition. On the other hand, if peak airflow occurs when significantly less than half of the air volume has been exhaled, this method would suggest that the patient has a relatively high likelihood of having an obstructive respiratory condition.

One method of quantitatively analyzing the expiration portion of a flow/volume loop based on the peak of the expiration portion involves calculating a peak ratio. Calculating a peak ratio can be illustrated with reference to FIGS. 1B and 2B. For purposes of illustration, only rough values are used. The first step in calculating a peak ratio is to determine the volume value that corresponds to the peak. In FIG. 1B, the peak volume value is approximately −5.0 mL. In FIG. 2B, the peak volume value is approximately −1.5 mL. The next step is to determine the volume values for the full-inhale and full-exhale points. In FIG. 1B, the volume value for the full-inhale point 40 is approximately −10 mL, and the volume value for the full-exhale point 25 is approximately 1.25 mL. In FIG. 2B, the volume value for the full-inhale point 230 is approximately −6.5 mL, and the volume value for the full-exhale point 225 is approximately 12 mL. With the volume values for the full-inhale point, the peak point, and the full-exhale point, a peak ratio can be calculated according to the following formula:

$$PR = \frac{V_p - V_{fi}}{V_{fe} - V_{fi}}$$

where PR=the peak ratio, $V_p$=the volume value at the peak point, $V_{fi}$=the volume value at the full-inhale point, and $V_{fe}$=the volume value at the full-exhale point. According to this formula, the peak ratio for the expiration portion of FIG. 1B is 0.44, and the peak ratio for the expiration portion of FIG. 2B is 0.27. A peak ratio of 0.5 would mean that the peak occurred when exactly half of the air volume had been exhaled. In many instances, peak ratios are based on the amount of time that has elapsed since the beginning of expiration. For example, the peak ratio can be a ratio of (a) the time difference between the beginning of expiration and when the flow value reaches its peak to (b) the entire duration of expiration. Whether a peak ratio is indicative of a normal condition or an obstructive respiratory condition depends on the age and size of the patient and can be determined with reference to standard values from a representative population.

Using the peak of the expiration portion to quantitatively analyze a flow/volume loop can have drawbacks in assessing a patient's respiratory condition. In the flow/volume loops of FIGS. 1B and 2B, the peak of the expiration portion is generally indicative of the overall shape of the expiration portion. In many other instances, however, the peak of the expiration portion is not indicative of the overall shape of the expiration portion. Generally speaking, peak-based methods of quantitatively analyzing the expiration portion of flow/volume loops fail to use the full amount of information contained in the expiration portion.

Figure 3A:
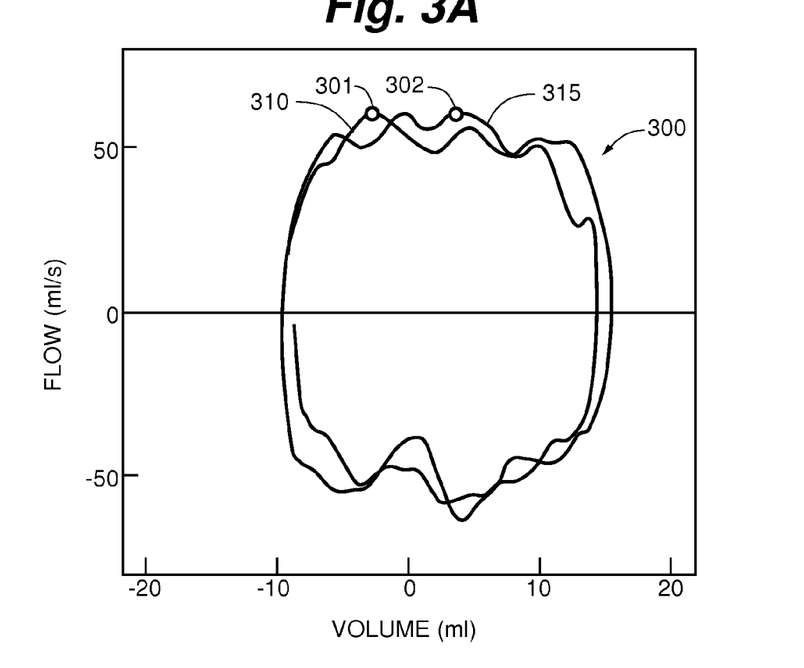
FIG. 3A is an illustrative flow/volume loop showing data from two consecutive respiratory cycles for a healthy example patient.

FIG. 3A shows an example of a flow/volume loop in which the peak of the expiration portion is not indicative of the overall shape of the expiration portion. FIG. 3A shows a plot 300 of two consecutive breathing cycles for a healthy example patient. The first cycle is represented by flow/volume loop 310, and the second cycle is represented by flow/volume loop 315. The peak flow value of the first-cycle flow/volume loop 310 is marked point 301. The peak flow value of the second-cycle flow/volume loop 315 is marked point 302. As can be seen, the volume values for the two peaks 301 and 302 differ significantly. In fact, the peak ratio of the first-cycle flow/volume loop 310 is 0.35 while the peak ratio of the second-cycle flow/volume loop 315 is 0.55. These two peak ratios fall on opposite sides of the dividing line that separates generally normal respiratory conditions from obstructive respiratory conditions for the healthy example patient. Though the example patient corresponding to FIG. 3A has a normal respiratory condition, if a clinician based his/her assessment of the patient's respiratory condition on the peak of the expiration portion of the first-cycle flow/volume loop 310, his/her assessment would be wrong.

One important difference between the flow/volume loops of FIGS. 1B and 2B and those of FIG. 3A involves their respective smoothness. In FIGS. 1B and 2B, the expiration portions are relatively smooth from full inhale to full exhale.

In contrast, the flow/volume loops 310, 315 of FIG. 3A are relatively jagged on both the inspiration and expiration portions. The bumps are due to noise within the measurement system. The noise influences the measurement of the flow data and/or the volume data. The effect on the measured flow data or volume data is then magnified when calculating either the flow data from measured volume data or vice versa. For example, such noise often appears in recordings made from volume data where flow has been calculated by differentiation of the volume signal. This noise can result in a peak that varies widely from cycle to cycle and that is not indicative of the overall shape of the expiration portion. The noise is especially noteworthy in the flow/volume loops 310, 315 of FIG. 3A because the expiration portions are relatively flat for a significant percentage of expiration, meaning that an arbitrary blip caused by noise anywhere along the flat stretch can end up being the peak. In many cases, the unpredictability of the peak location from one respiratory cycle to the next significantly impedes the clinician from extracting the useful diagnostic information from the expiration portion of the flow/volume loop.

Figure 3B:
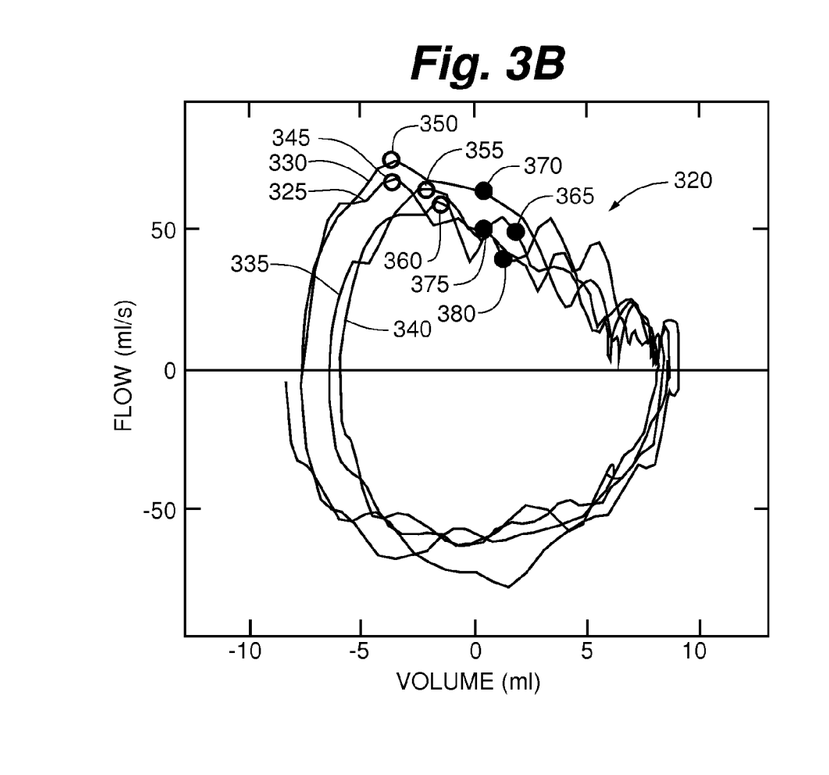
FIG. 3B is an illustrative flow/volume loop showing data from four consecutive respiratory cycles for an example patient with an obstructive respiratory condition.

The drawbacks of quantitatively analyzing the expiration portions of flow/volume loops by the location of the peak have been recognized, and attempts to mitigate those drawbacks have been made. One such attempt involves comparing the peak with flow values at certain predetermined volume percentages. For example, some methods involve comparing the peak flow value with the flow value at the point when 50% (and/or 75%) of the air volume has been exhaled. FIG. 3B shows another example of a flow/volume loop in which the peak of the expiration portion is not indicative of the overall shape of the expiration portion. FIG. 3B shows a plot 320 of four consecutive breathing cycles for an example patient with an obstructive respiratory condition. The first cycle is marked by flow/volume loop 325, the second cycle is marked by flow/volume loop 330, the third cycle is marked by flow/volume loop 335, and the fourth cycle is marked by flow/volume loop 340. The expiration portion peaks for the respective flow/volume loops 325, 330, 335, 340 are as follows: point 345 is for flow/volume loop 325, point 350 is for flow/volume loop 330, point 355 is for flow/volume loop 335, and point 360 is for flow/volume loop 340. Additionally, the points at 50% of the expired volumes for the respective flow/volume loops 325, 330, 335, 340 are as follows: point 365 is for flow/volume loop 325, point 370 is for flow/volume loop 330, point 375 is for flow/volume loop 335, and point 380 is for flow/volume loop 340.

A ratio of the flow value at 50% of the expired volume to the expiration portion peak flow value is a common way of comparing the expiration portion peak flow value to the flow value at 50% of the expired volume. Whether this ratio is indicative of a normal condition or an obstructive respiratory condition depends on the age and size of the patient and can be determined with reference to standard values from a representative population. This ratio for the four flow/volume loops 325, 330, 335, 340 of FIG. 3B ranged from 0.47 to 0.86. This degree of variability from one cycle to the next significantly undermines confidence in the resulting information, thereby impeding the clinician from extracting the useful diagnostic information from the expiration portion of the flow/volume loop.

Even these attempts to improve the peak-based methods of quantitatively analyzing the expiration portions of flow/volume loops have proven unsatisfactory. Because the peak of the expiration portion of a flow/volume loop is often not indicative of the overall shape of the expiration portion, methods of quantitatively analyzing expiration portions based only on the peak are inadequate for providing clinicians the information contained in the expiration portion.

A better way of quantitatively analyzing the expiration portion of a flow/volume loop involves defining the space under the expiration portion and analyzing the shape of that space. If the overall shape of the expiration space is unbalanced to the left, the patient may have an obstructive respiratory condition. If the overall shape of the expiration space is generally balanced or symmetrical, the patient likely does not have an obstructive respiratory condition. Methods of quantitatively analyzing expiration portions of flow/volume loops based on the overall shape of the expiration space are significantly less susceptible to measurement noise, meaning that the results are more repeatable, more robust, and generally more reliable than other methods.

Figure 4:
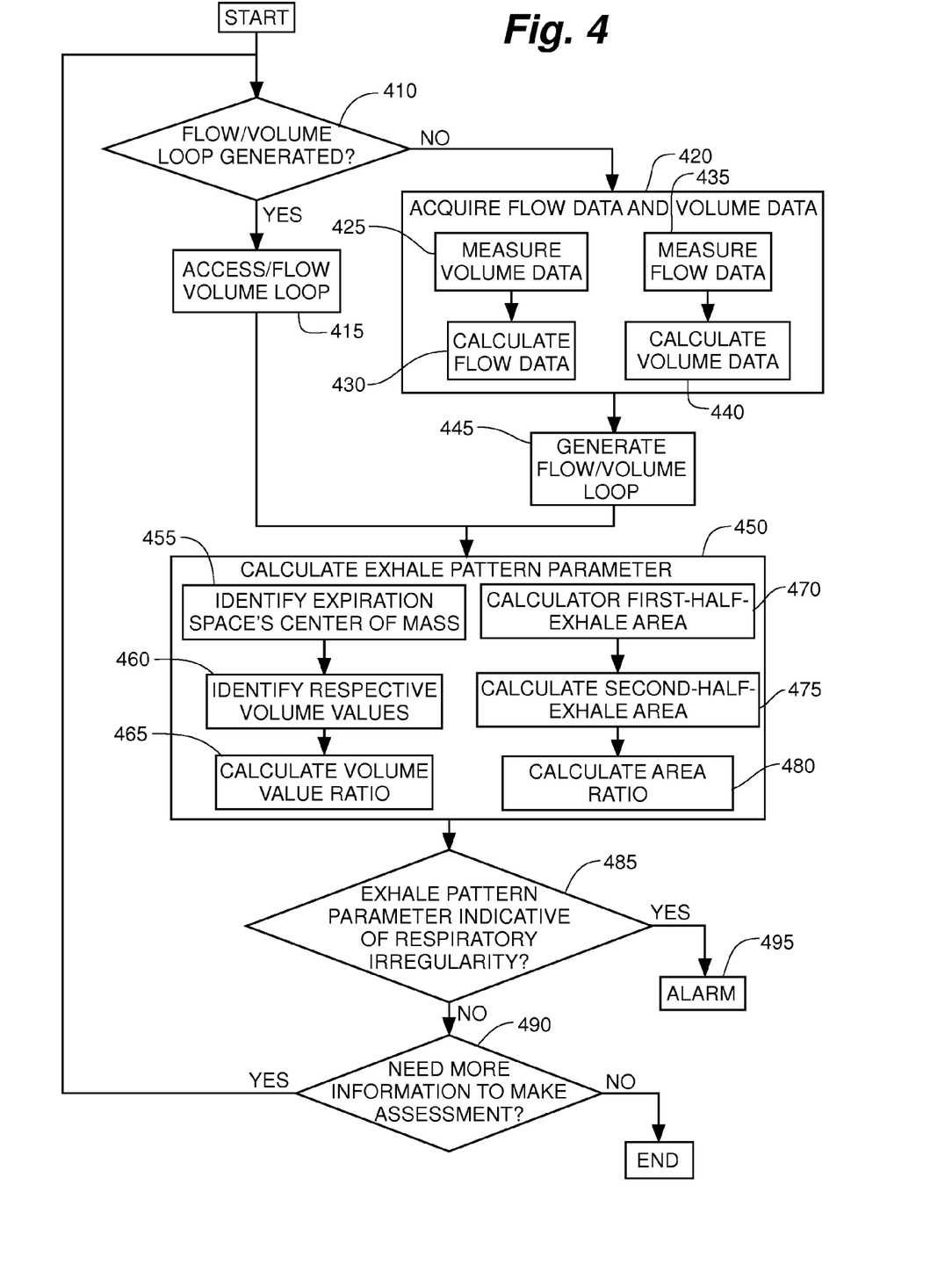
FIG. 4 is a flow chart of an illustrative method of gathering data related to breathing patterns of a patient, according to embodiments of the present invention.

FIG. 4 shows a method of gathering data related to breathing patterns of a patient using an expiration-space-based technique, rather than a peak-based technique, to analyze the expiration portion. In some embodiments, a computer-readable medium can be programmed with instructions for causing a programmable processor to perform the method of FIG. 4. Generally speaking, the method involves quantitatively analyzing a flow/volume loop and making a determination whether that flow/volume loop is indicative of an obstructive respiratory condition.

Some embodiments operate in connection with already-existing flow/volume loops, while some embodiments involve first generating a flow/volume loop and then analyzing it. To that end, as can be seen, an initial question is whether a flow/volume loop has already been generated (410). If it has, that flow/volume loop can be accessed (415). If a flow/volume loop has not yet been generated, steps can be taken to generate one. To generate a flow/volume loop, flow data and volume data can be acquired (420). As noted elsewhere herein, the flow data can relate to a rate of air flow into and out of the patient's lungs and the volume data can relate to changes in volume of the patient's lungs. As also noted elsewhere herein, acquiring flow data and volume data can include measuring volume data (425) and calculating flow data from measured volume data (430) or measuring flow data (435) and calculating volume data from measured flow data (440). A flow/volume loop can then be generated (445) with flow data and volume data that have been acquired.

Whether accessing an already existing flow/volume loop or generating one based on acquired flow data and volume data, the flow/volume loop can generally have the properties discussed in connection with FIG. 1B. Referring to FIG. 1B, the flow/volume loop 35 can have an expiration portion 45 and an inspiration portion 50. The expiration portion 45 can begin with a full-inhale point 40 and end with a full-exhale point 25. Both the full-inhale point 40 and the full-exhale point 25 lie along a zero-flow line 37. In some cases, the flow data and the volume data on which the flow/volume loop 35 is based can include average flow data and average volume data from multiple patient breathing cycles.

Referring again to FIG. 4, with the flow/volume loop generated or accessed, an exhale pattern parameter can be calculated based on an overall shape of an expiration space (450). The expiration space, or the space under the expiration portion of the flow/volume loop, can be bounded by the expiration portion of the flow/volume loop and the zero-flow line. Quantitatively analyzing various characteristics of this space using the full amount of information contained therein can yield significantly more useful information to a clinician regarding the patient's respiratory condition than analyzing the location of the expiration portion's peak. One or more blips in the expiration portion caused by measurement noise (see FIGS. 3A-3B and corresponding discussion) will not have a significant effect on the overall shape of the expiration portion.

In preferred embodiments of the present invention, an exhale pattern parameter is a way of characterizing the overall shape of the expiration space. Two primary types of exhale pattern parameters are discussed herein: those based on the expiration space's center of mass and those based on the area of the expiration space for the first volume half of expiration relative to the area of the expiration space for the second volume half of expiration. It should be understood, however, that there are many other ways to calculate an expiration pattern parameter based on the overall shape of the expiration portion, each of which fall within the scope of embodiments of the present invention.

As noted, one type of exhale pattern parameter discussed herein is based on the expiration space's center of mass. Referring again to FIG. 4, in such embodiments, the expansion space's center of mass can first be identified (455). The center of mass can have a corresponding flow value and volume value, which depend on the location of the center of mass. For purposes of some embodiments of the present invention, the volume value corresponding to the center of mass can be important. Volume values can be identified, with the full-inhale point corresponding to a full-inhale volume value, the full-exhale point corresponding to a full-exhale volume value, and the center of mass of the expiration space corresponding to a center-of-mass volume value (460). The full-inhale volume value and the full-exhale volume value are often readily identifiable with reference to the flow/volume loop. In some embodiments, the center-of-mass volume value can be calculated according to the following formula:

$$CM_V = \frac{\int_{t_{fi}}^{t_{fe}} V(t) \cdot [F(t)]^2 \, dt}{\int_{t_{fi}}^{t_{fe}} [F(t)]^2 \, dt}$$

wherein $CM_V$=the center-of-mass volume value; $t_{fi}$=time at the full-inhale point; $t_{fe}$=time at the full-exhale point; V(t)= exhaled volume as a function of time; and F(t)=air flow as a function of time. In some embodiments, the center-of-mass volume value can be based on discrete sample points representing measured values taken at equidistant points in time according to the following formula:

$$CM_V \approx \frac{\sum_{p=n_{fi}}^{n_{fe}} (V_p F_p^2)}{\sum_{p=n_{fi}}^{n_{fe}} F_p^2}$$

wherein $CM_V$=the center-of-mass volume value; $n_{fi}$ is a sample point count number at the full-inhale point; $n_{fe}$ is a sample point count number at the full-exhale point; and V and F are sample point series describing volume and flow waveforms.

In many embodiments, the exhale pattern parameter can be based on the full-inhale volume value, the full-exhale volume value, and the center-of-mass volume value. In some embodiments, the exhale pattern parameter is a volume value ratio, and the next step is to calculate the volume value ratio (465).

Figure 5A:
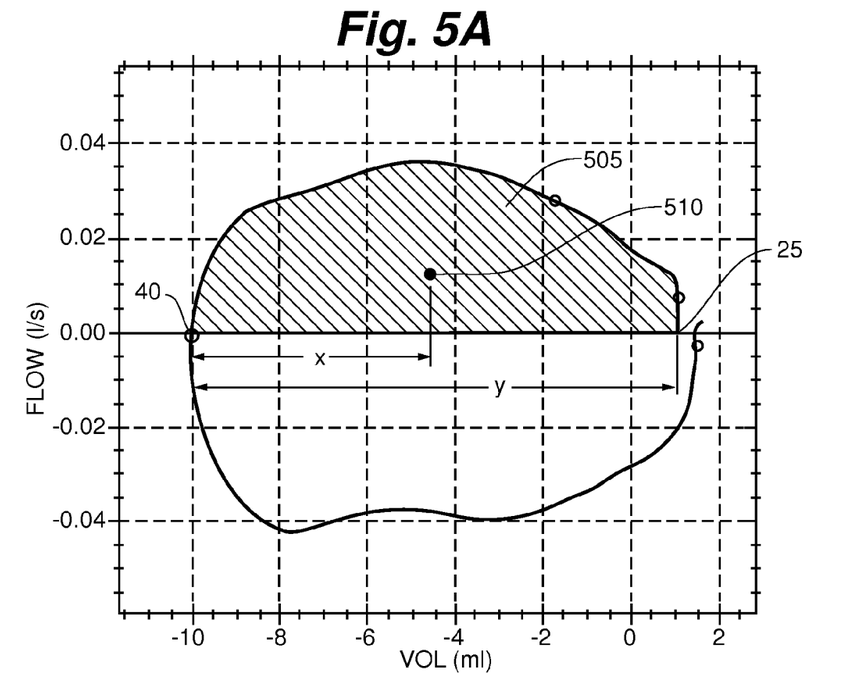
FIG. 5A is the flow volume of FIG. 1B, with annotations that help illustrate methods according to embodiments of the present invention.
Figure 5B:
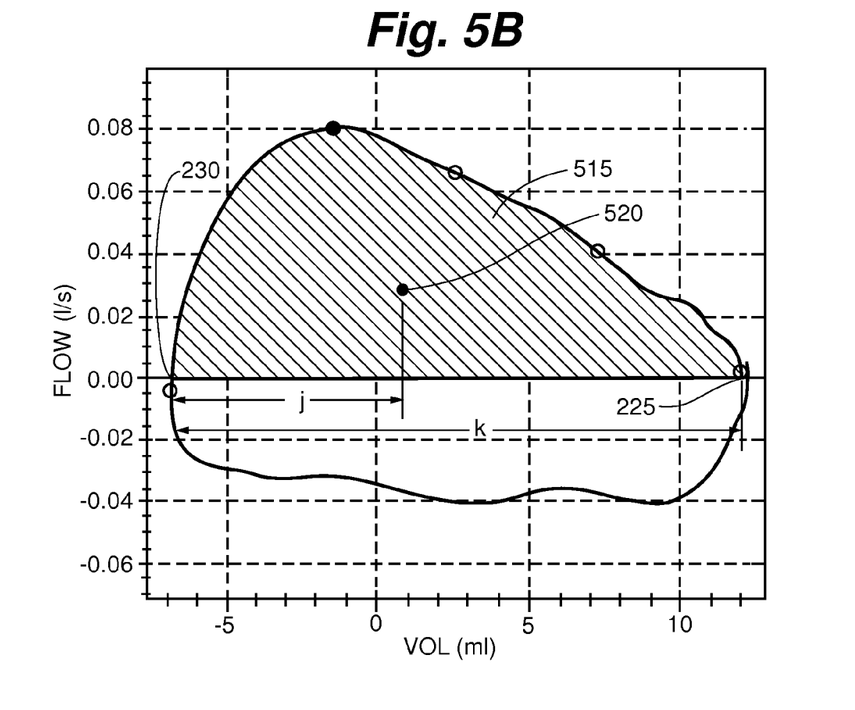
FIG. 5B is the flow volume of FIG. 2B, with annotations that help illustrate methods according to embodiments of the present invention.

Calculating the volume value ratio is illustrated with reference to FIGS. 5A-5B. FIGS. 5A-5B show reproductions of the flow/volume loops of FIGS. 1B and 2B, respectively, annotated for purposes of illustrating the calculation of a volume value ratio. FIG. 5A includes a full-inhale point 40 and a full-exhale point 25, with the expiration space shaded in and marked with reference number 505. The center of mass of the expiration space 505 is marked with reference number 510. As shown, x is the difference between the center-of-mass volume value and the full-inhale volume value, and y is the difference between the full-exhale volume value and the full-inhale volume value. FIG. 5B is likewise marked with a full-inhale point 230, a full-exhale point 225, the expiration space 515, the center of mass 520, the difference between the center-of-mass volume value and the full-inhale volume value j, and the difference between the full-exhale volume value and the full-inhale volume value k.

In many embodiments, the volume value ratio is a ratio of (i) a difference between the center-of-mass volume value and the full-inhale volume value to (ii) a difference between the full-exhale volume value and the full-inhale volume value. For FIG. 5A, the volume value ratio is x/y, and for FIG. 5B, the volume value ratio is j/k.

The flow/volume loop shown in FIG. 5A (and FIG. 1B) represents volume data and flow data from a healthy, 3.5-kilogram, full-term infant. The volume value ratio for this patient was 0.48. The flow/volume loop shown in FIG. 5B (and FIG. 2B) represents volume data and flow data from a 2.0-kilogram, pre-term infant who was recovering from assisted ventilation therapy. The volume value ratio for this patient was 0.41.

The volume value ratio for a given expiration portion of a flow/volume loop is significantly more repeatable than the expiration portion's peak. For example, referring to FIG. 3A, the volume value ratio for the first-cycle flow/volume loop 310 is 0.505, and the volume value ratio for the second-cycle flow/volume loop 315 is 0.508. In contrast, the temporal position of the peaks (time to peak) relative to the duration of the expiratory phase are 35% and 55%. Additionally, in an example referring to FIG. 3B, the volume value ratio for the four flow/volume loops 325, 330, 335, 340 ranged from 0.45 to 0.45, while the ratio of expiration portion peak flow value to flow value at 50% of the expired volume for the same four flow/volume loops 325, 330, 335, 340 ranged from 0.47 to 0.86.

Referring again to FIG. 4, as noted above, another type of exhale pattern parameter discussed herein is based on the area of the expiration space for the first half of expiration relative to the area of the expiration space for the second half of expiration. This is generally represented in steps (470), (475), and (480). First, the first-half-exhale area can be calculated (470), and the second-half-exhale area can be calculated (475).

Figure 6A:
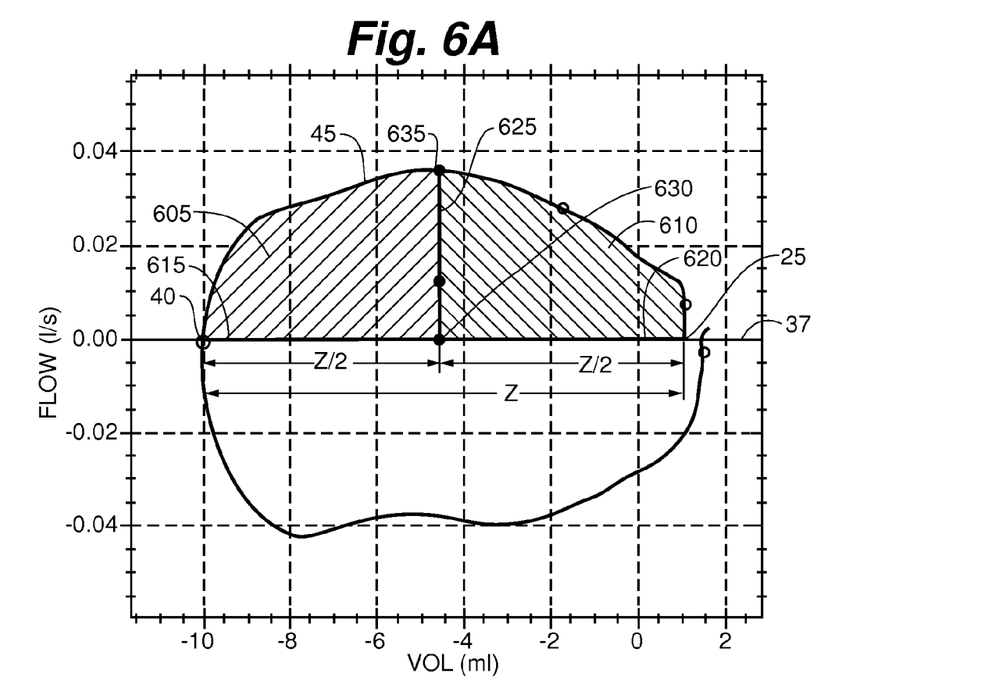
FIG. 6A is the flow volume of FIG. 1B, with annotations that help illustrate methods according to embodiments of the present invention.
Figure 6B:
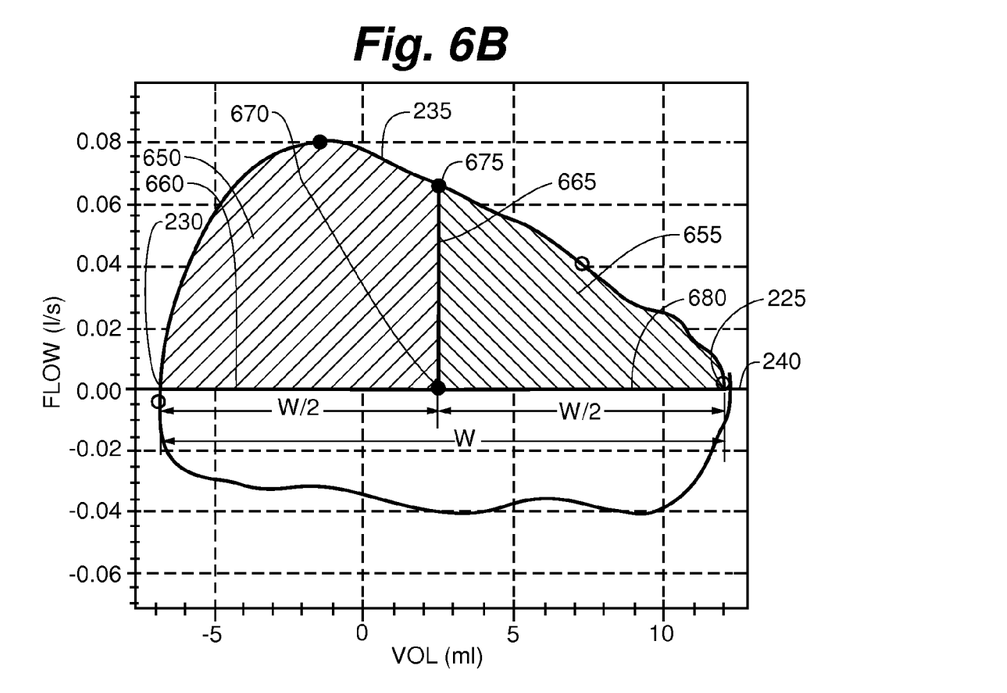
FIG. 6B is the flow volume of FIG. 2B, with annotations that help illustrate methods according to embodiments of the present invention.

FIGS. 6A-6B help illustrate how the first-half-exhale area and the second-half exhale area are calculated. Like FIGS. 5A-5B, FIGS. 6A-6B are reproductions of the flow/volume loops of FIGS. 1B and 2B, respectively, annotated for purposes of illustrating calculation of this type of exhale pattern parameter. FIG. 6A includes a full-inhale point 40 and a full-exhale point 25. The first-half-exhale area is the area of the space shaded in and marked 605, and the second-half-exhale area is the area of the space shaded in and marked 610. As can be seen, space 605 combined with space 610 makes up the expiration space. Space 605 is bounded by the expiration portion 45, line segment 615, and line segment 625. Line segment 615 extends between the full-inhale point 40 and the half-exhale point 630 along the zero-flow line 37. Line segment 625 extends perpendicularly to the zero-flow line 37 between the half-exhale point 630 and a corresponding point 635 on the expiration portion 45 of the flow/volume loop. Space 610 is bounded by the expiration portion 45, line segment 625, and line segment 620, with line segment 620 extending between the half-exhale point 630 and the full-exhale point 25 along the zero-flow line 37.

FIG. 6B includes a full-inhale point 230 and a full-exhale point 225. The first-half-exhale area is the area of the space shaded in and marked 650, and the second-half-exhale area is the area of the space shaded in and marked 655. As can be seen, space 650 combined with space 655 makes up the expiration space. Space 650 is bounded by the expiration portion 235, line segment 660, and line segment 665. Line segment 660 extends between the full-inhale point 230 and the half-exhale point 670 along the zero-flow line 240. Line segment 665 extends perpendicularly to the zero-flow line 240 between the half-exhale point 670 and a corresponding point 675 on the expiration portion 235 of the flow/volume loop. Space 655 is bounded by the expiration portion 235, line segment 665, and line segment 680, with line segment 680 extending between the half-exhale point 670 and the full-exhale point 225 along the zero-flow line 240.

The first-half-exhale area and the second-half-exhale area can be calculated in a variety of ways. In some embodiments, the first-half-exhale area can be calculated according to the following formula:

$$A_{fh} = \int_{t_{fi}}^{t_{he}} [F(t)]^2 dt$$

wherein $A_{fh}$=the first-half-exhale area; $t_{fi}$=time at the full-inhale point; $t_{he}$=time at the half-exhale point; and F(t)=air flow as a function of time. In some embodiments, calculating the first-half-exhale area can be based on discrete sample points representing measured values taken at equidistant points in time according to the following formula:

$$A_{fh} \approx \Delta t \sum_{p=n_{fi}}^{n_{he}} F_p^2$$

wherein $A_{fh}$=the first-half-exhale area; $\Delta t$=a time interval between the equidistant points in time; $n_{fi}$ is a sample point count number at the full-inhale point; $n_{he}$ is a sample point count number at the half-exhale point; and F is a sample point series describing a flow waveform. In some embodiments, the second-half-exhale area can be calculated according to the following formula:

$$A_{sh} = \int_{t_{he}}^{t_{fe}} [F(t)]^2 dt$$

wherein $A_{sh}$=the second-half-exhale area; $t_{he}$=time at the half-exhale point; $t_{fe}$=time at the full-exhale point; and F(t)= air flow as a function of time. In some embodiments, calculating the second-half-exhale area can be based on discrete sample points representing measured values taken at equidistant points in time according to the following formula:

$$A_{sh} \approx \Delta t \sum_{p=n_{he}+1}^{n_{fe}} F_p^2$$

wherein $A_{sh}$=the second-half-exhale area; $\Delta t$=a time interval between the equidistant points in time; $n_{he}$ is a sample point count number at the half-exhale point; $n_{fe}$ is a sample point count number at the full-exhale point; and F is a sample point series describing a flow waveform.

Referring again to FIG. 4, with the first-half-exhale area and the second-half-exhale area calculated (470), (475), the exhale pattern parameter can be based on a first-half-exhale area and a second-half-exhale area. In some embodiments, the exhale pattern parameter is an area ratio, and the next step is to calculate the area ratio (480). In many embodiments, the area ratio can be a ratio of the first-half-exhale area to the first-half-exhale area plus the second-half-exhale area.

The flow/volume loop shown in FIG. 6A (and FIGS. 1B and 5A) represents volume data and flow data from a healthy, 3.5-kilogram, full-term infant. The area ratio for this patient was 0.48. The flow/volume loop shown in FIG. 6B (and FIGS. 2B and 5B) represents volume data and flow data from a 2.0-kilogram, pre-term infant who was recovering from assisted ventilation therapy. The area ratio for this patient was 0.37.

The types of, and methods of calculating, exhale pattern parameters discussed herein are only illustrative. Other suitable methods of calculating exhale pattern parameters based on the overall shape of the expiration portion are within the scope of embodiments of the present invention. For example, a vertical line dividing the area of the expiration space in half can be determined and an exhale pattern parameter can be based on one or more characteristics of that line. Additionally, exhale pattern parameters based on the expiration space's center of mass, other than the volume value ratio discussed herein, are within the scope of embodiments of the present invention, as are exhale pattern parameters based on the first-half-exhale area and the second-half-exhale area that do not involve the area ratio discussed herein.

Referring again to FIG. 4, with the exhale pattern parameter calculated (450), a determination can be made whether the exhale pattern parameter is indicative of a respiratory irregularity (485). The exhale pattern parameter can be compared to a predetermined parameter to determine whether the volume data and/or the flow data are indicative of a respiratory irregularity. If the exhale pattern parameter includes a volume value ratio (discussed above), a determination can be made whether the volume value ratio is less than a predetermined threshold ratio, the predetermined threshold ratio being indicative of a respiratory irregularity. In some such embodiments, the predetermined threshold ratio is approximately 0.45. As noted above, the volume value ratio for the healthy, full-term infant discussed in connection with FIGS. 1A-1B and 5A was 0.48, meaning that this method rightly determined that the infant has no respiratory irregularity. Additionally, the volume value ratio for the pre-term infant discussed in connection with FIGS. 2A-2B and 5B was 0.41, meaning that this method rightly determined that the infant likely has a respiratory irregularity. If the exhale pattern parameter includes an area ratio, a determination can be made whether the area ratio is less than a predetermined threshold ratio, the predetermined threshold ratio being indicative of a respiratory irregularity. In some such embodiments, the predetermined threshold ratio is approximately 0.45. As noted above, the area ratio for the healthy, full-term infant discussed in connection with FIGS. 1A-1B, 5A, and 6A was 0.48, meaning that this method rightly determined that the infant has no respiratory irregularity. Additionally, the area ratio for the pre-term infant discussed in connection with FIGS. 2A-2B, 5B, and 6B was 0.37, meaning that this method rightly determined that the infant likely has a respiratory irregularity.

If it is determined that the exhale pattern parameter is indicative of a respiratory irregularity (485), the condition can be flagged for the clinician (495). The clinician can take appropriate measures, such as conducting further testing or initiating therapy. If it is determined that the exhale pattern parameter is not indicative of a respiratory irregularity (485), a determination is made whether the clinician needs more information to make a complete assessment (490). If more information is needed, one or more steps in the method can be repeated until the clinician is satisfied with the information produced by the method. When the determination is made that no more information is needed to make an assessment, the method can come to an end.

The order of steps provided in the method shown in FIG. 4 is provided for purposes of illustration only, and other orders that achieve the functionality recited are within the scope of embodiments of the present invention. Any of the functionality discussed herein may be implemented in the method shown in FIG. 4.

Various implementations of the systems and methods described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications, or code) include machine instructions for a programmable processor, and can be implemented in a high-level procedural and/or object-oriented programming language, and/or in assembly/machine language. As used herein, the term "compute-readable medium" refers to any computer program product, apparatus and/or device (e.g., magnetic discs, optical disks, memory, Programmable Logic Devices (PLDs)) used to provide instructions and/or data to a programmable processor, including a computer-readable medium that receives instructions as a computer-readable signal. The term "computer-readable signal" refers to any signal used to provide instructions and/or data to a programmable processor.

In the foregoing detailed description, the invention has been described with reference to specific embodiments. However, it may be appreciated that various modifications and changes can be made without departing from the scope of the invention as set forth in the appended claims. Thus, some of the features of preferred embodiments described herein are not necessarily included in preferred embodiments of the invention which are intended for alternative uses.

What is claimed is:

1. A non-transitory computer-readable medium programmed with instructions for performing a method of gathering data related to breathing patterns of a patient, the medium comprising instructions for causing a programmable processor to:

(a) access a flow/volume loop that displays flow data and volume data, the flow data relating to a rate of air flow into and out of the patient's lungs and the volume data relating to changes in volume of the patient's lungs, wherein the flow/volume loop includes an expiration portion and an inspiration portion, the expiration portion beginning with a full-inhale point and ending with a full-exhale point, which both lie along a zero-flow line; and (b) calculate an exhale pattern parameter comprising calculating a center-of-mass volume value from an overall shape of an expiration space, which is bounded by the expiration portion of the flow/volume loop and the zero-flow line.

2. The computer-readable medium of claim 1, wherein the flow data and the volume data comprises average flow data and average volume data from multiple patient breathing cycles.

3. The computer-readable medium of claim 1, further comprising instructions for causing the programmable processor to: (c) compare the exhale pattern parameter to a predetermined parameter to determine whether the volume data and/or the flow data are indicative of a respiratory irregularity.

4. The computer-readable medium of claim 1, wherein the full-inhale point corresponds to a full-inhale volume value, the full-exhale point corresponds to a full-exhale volume value, and the center of mass of the expiration space corresponds to a center-of-mass volume value and wherein the exhale pattern parameter is based on the full-inhale volume value, the full-exhale volume value, and the center-of-mass volume value.

5. The computer-readable medium of claim 4, wherein the center-of-mass volume value is calculated according to the following formula:

$$CM_V = \frac{\int_{t_{fi}}^{t_{fe}} V(t) \cdot [F(t)]^2 \, dt}{\int_{t_{fi}}^{t_{fe}} [F(t)]^2 \, dt}$$

wherein $CM_V$=the center-of-mass volume value; $t_{fi}$=time at the full-inhale point; $t_{fe}$=time at the full-exhale point; $V(t)$=exhaled volume as a function of time; and $F(t)$=air flow as a function of time.

6. The computer-readable medium of claim 4, wherein the center-of-mass volume value is based on discrete sample points representing measured values taken at equidistant points in time according to the following formula:

$$CM_V \approx \frac{\sum_{p=n_{fi}}^{n_{fe}} (V_p F_p^2)}{\sum_{p=n_{fi}}^{n_{fe}} F_p^2}$$

wherein $CM_V$=the center-of-mass volume value; $n_{fi}$ is a sample point count number at the full-inhale point; $n_{fe}$ is a sample point count number at the full-exhale point; and V and F are sample point series describing volume and flow waveforms.

7. The computer-readable medium of claim 4, wherein the exhale pattern parameter comprises a volume value ratio of (i) a difference between the center-of-mass volume value and the full-inhale volume value to (ii) a difference between the full-exhale volume value and the full-inhale volume value.

8. The computer-readable medium of claim 7, further comprising (d) determining whether the volume value ratio is less than a predetermined threshold ratio, the predetermined threshold ratio being indicative of a respiratory irregularity.

9. The computer-readable medium of claim 8, wherein the predetermined threshold ratio is approximately 0.45.

10. A non-transitory computer-readable medium programmed with instructions for performing a method of gathering data related to breathing patterns of a patient, the medium comprising instructions for causing a programmable processor to:

(a) access a flow/volume loop that displays flow data and volume data, the flow data relating to a rate of air flow into and out of the patient's lungs and the volume data relating to changes in volume of the patient's lungs, wherein the flow/volume loop includes an expiration portion and an inspiration portion, the expiration portion beginning with a full-inhale point and ending with a full-exhale point, which both lie along a zero-flow line; and (b) calculate an exhale pattern parameter based on an overall shape of an expiration space, which is bounded by the expiration portion of the flow/volume loop and the zero-flow line, wherein a half-exhale point lies on the zero-flow line halfway between the full-inhale point and the full-exhale point and wherein the instructions for causing the programmable processor to calculate the exhale pattern parameter comprise instructions for causing the programmable processor to:

(i) calculate a first-half-exhale area, the first-half-exhale area being the area of a shape bounded by (A) the expiration portion, (B) a first line segment that extends between the full-inhale point and the half-exhale point along the zero-flow line, and (C) a second line segment that extends perpendicularly to the zero-flow line between the half-exhale point and a corresponding point on the expiration portion of the flow/volume loop, (ii) calculate a second-half-exhale area, the second-half-exhale area being the area of a shape bounded by (A) the expiration portion, (B) the second line segment, and (C) a third line segment that extends between the half-exhale point and the full-exhale point along the zero-flow line, and (iii) determine the exhale pattern parameter based on the first-half-exhale area and the second-half-exhale area.

11. The computer-readable medium of claim 10, wherein the instructions for causing the programmable processor to calculate the first-half-exhale area comprise instructions for causing the programmable processor to use the following formula:

$$A_{fh} = \int_{t_{fi}}^{t_{he}} [F(t)]^2 \, dt$$

and the instructions for causing the programmable processor to calculate the second-half-exhale area comprise instructions for causing the programmable processor to use the following formula:

$$A_{sh} = \int_{t_{he}}^{t_{fe}} [F(t)]^2 \, dt$$

wherein $A_{fh}$=the first-half-exhale area; $A_{sh}$=the second-half-exhale area; $t_{fi}$=time at the full-inhale point; $t_{he}$ =time at the half-exhale point; $t_{fe}$=time at the full-exhale point; and F(t)= air flow as a function of time.

12. The computer-readable medium of claim 10, wherein the instructions for causing the programmable processor to calculate the first-half-exhale area comprise instructions for causing the programmable processor to use discrete sample points representing measured values taken at equidistant points in time according to the following formula:

$$A_{fh} \approx \Delta t \sum_{p=n_{fi}}^{n_{he}} F_p^2$$

and the instructions for causing the programmable processor to calculate the second-half-exhale area comprise instructions for causing the programmable processor to use discrete sample points representing measured values taken at equidistant points in time according to the following formula:

$$A_{sh} \approx \Delta t \sum_{p=n_{he}+1}^{n_{fe}} F_p^2$$

wherein $A_{fh}$=the first-half-exhale area; $A_{sh}$=the second-half-exhale area; $\Delta t$=a time interval between the equidistant points in time; $n_{fi}$ is a sample point count number at the full-inhale point; $n_{he}$ is a sample point count number at the half-exhale point; $n_{fe}$ is a sample point count number at the full-exhale point; and F is a sample point series describing a flow waveform.

13. The computer-readable medium of claim 10, wherein the instructions for causing the programmable processor to calculate the exhale pattern parameter comprise instructions for causing the programmable processor to calculate an area ratio of the first-half-exhale area to the first-half-exhale area plus the second-half-exhale area, the exhale pattern parameter comprising the area ratio.

14. The computer-readable medium of claim 13, further comprising instructions for causing the programmable processor to (c) determine whether the area ratio is less than a predetermined threshold ratio, the predetermined threshold ratio being indicative of a respiratory irregularity.

15. The computer-readable medium of claim 13, wherein the predetermined threshold ratio is approximately 0.45.

* * * * *